United States Patent [19]
Nilssen

[11] Patent Number: 5,614,802
[45] Date of Patent: Mar. 25, 1997

[54] FREQUENCY, VOLTAGE AND WAVESHAPE CONVERTER FOR A THREE PHASE INDUCTION MOTOR

[76] Inventor: Ole K. Nilssen, 408 Caesar Dr., Barrington, Ill. 60010

[21] Appl. No.: 8,093

[22] Filed: Jan. 22, 1993

Related U.S. Application Data

[63] Continuation of Ser. No. 643,169, Jan. 22, 1991, abandoned, which is a continuation of Ser. No. 243,246, Sep. 8, 1988, abandoned, which is a continuation of Ser. No. 14,353, Feb. 13, 1987, abandoned.

[51] Int. Cl.$^6$ ........................................................ H02P 7/00
[52] U.S. Cl. ........................................................ 318/800
[58] Field of Search ........................................ 318/800, 807, 318/801, 811; 363/41, 97, 98

[56] References Cited

U.S. PATENT DOCUMENTS

| | | | |
|---|---|---|---|
| 3,334,292 | 8/1967 | King et al. | 363/41 |
| 3,509,445 | 4/1970 | Chirgwin et al. | 363/41 |
| 3,584,279 | 6/1971 | Krauthamer | 318/808 |
| 4,466,052 | 8/1984 | Thrap | 363/41 |
| 4,479,175 | 10/1984 | Gille et al. | 363/41 |
| 4,494,178 | 1/1985 | Ishima | 363/41 X |
| 4,507,724 | 3/1985 | Glennon | 363/41 |
| 4,520,437 | 5/1985 | Boettcher, Jr. et al. | 363/98 X |
| 4,564,895 | 1/1986 | Glennon | 363/41 |
| 4,581,693 | 4/1986 | Ueda et al. | 318/811 |
| 4,620,143 | 10/1986 | Matty | 318/811 |
| 4,626,979 | 12/1986 | JaQuay | 363/41 |
| 4,635,177 | 1/1987 | Shekhawat et al. | 363/132 |
| 4,670,828 | 6/1987 | Shekhawat et al. | 363/132 |
| 4,706,180 | 11/1987 | Wills | 363/98 X |
| 4,719,551 | 1/1988 | Nishizawa et al. | 363/41 |

OTHER PUBLICATIONS

Patel et al, "Generalized Techniques of Harmonic Elimination and Voltage Control in Thyristor Inverters: Part I–Harmonic Elemination", IEEE Transactions on Industry Applications, vol. IA–9, No. 3, May/Jun. 1973 pp. 310–317.

*Primary Examiner*—Anthony Wysocki

[57] ABSTRACT

A frequency, voltage and waveshape converter is placed between the terminals of an ordinary single-phase power line and the power input terminals of a three-phase induction motor. The converter is operable to provide to the power input terminals of the induction motor a three-phase AC voltage of frequency, magnitude and/or waveshape controllably different from those of the power line voltage, thereby to permit effective control of motor speed and power factor. The frequency of the AC voltage is adjustable over the range of 12–120 Hz, with the effective magnitude of the AC voltage being automatically adjusted in proportion therewith, thereby providing for a very wide range of motor speed control without incurring reduced motor operating efficiency.

13 Claims, 5 Drawing Sheets

FREQUENCY, VOLTAGE AND WAVESHAPE CONVERTER FOR A THREE PHASE INDUCTION MOTOR

This application is a continuation of Ser. No. 07/643,169 filed Jan. 22, 1991 abandoned, which is a continuation of Ser. No. 07/243,246 filed Sep. 8, 1988 abandoned, which is a continuation of Ser. No. 07/014,353 filed Feb. 13, 1987 abandoned.

BACKGROUND OF THE INVENTION

1. Field of Invention

The present invention relates to means operable: i) to be interposed between the power line and the power input terminals of a three-phase induction motor, and ii) to control the frequency, magnitude and/or waveshape of the voltage provided to the power input terminals of this three-phase induction motor.

2. Elements of Prior Art

A three-phase induction motor is basically a synchronous device. However, most commonly available means for controlling its speed are based on controlling the magnitude of the current supplied to the motor, thereby attaining but a very modest degree of speed control in return for a significant reduction in motor efficiency.

SUMMARY OF THE INVENTION

Objects of the Invention

An object of the present invention is that of providing an improved means for controlling the frequency, magnitude and/or waveshape of the three-phase voltage provided to a three-phase induction motor.

Another object is that of providing a means: i) adapted to be interposed between an ordinary electric utility power line and a three-phase induction motor, and ii) operative to provide a three-phase voltage to this motor, the frequency, magnitude and/or waveshape being controllably adjustable.

These as well as other objects, features and advantages of the present invention will become apparent from the following description and claims.

Brief Description

In its preferred embodiment, the present invention comprises a phase, frequency, magnitude and waveshape converter interposed between the 120 Volt/60 Hz voltage of an ordinary electric utility power line and the power input terminals of an ordinary three-phase induction motor intended for normal operation on three-phase 60 Hz power line voltage. The converter is controllably operable to provide to the these power input terminals a three-phase AC voltage of frequency, magnitude and waveshape controllably different from those of the 120 Volt/60 Hz power line voltage. In particular, by way of manually operable control means, the magnitude and the frequency of the three-phase AC voltage can be continuously adjusted between 24 Volt/12 Hz and 240 Volt/120 Hz, with the voltage-magnitude automatically increasing in proportion with the frequency.

The frequency, magnitude and waveshape converter consists of two sub-systems: i) a high power factor AC-to-DC converter connected with the power line and operative to provide at a DC output a DC voltage of substantially constant magnitude, and ii) a controllable DC-to-AC converter connected with the DC output and operative to provide at an AC output a three-phase AC voltage of adjustably controllable frequency, magnitude and waveshape.

The AC-to-DC converter comprises rectifier means operative to provide unfiltered full-wave-rectified power line voltage to a half-bridge inverter, the 30 kHz amplitude-modulated squarewave voltage output of which is connected across a series-resonant L-C circuit.

The 30 kHz current available from across the tank-capacitor of the L-C circuit is rectified and applied to an energy-storing capacitor means, the output of which is a DC voltage of an adjustable but, once adjusted, substantially constant magnitude.

Due to the basic nature of the series-resonant L-C circuit, the energy-storing capacitor means will be charged with a current of instantaneous absolute magnitude roughly proportional to that of the inverter's squarewave output voltage. As a result, the current drawn from the power line by the AC-to-DC converter is drawn with a high power factor.

The DC-to-AC converter consists of three half-bridge inverters, each operative to be powered from the constant-magnitude DC voltage and to provide an output voltage of independently controllable frequency and relative symmetry (ON/OFF times). Each of these pulse-ratio-modulated squarewave output voltages is then fed through an inductive averaging means and provided in the form of an AC output voltage to one of the three power input terminals of the three-phase induction motor.

For each half-bridge inverter, a comparator means is operative to compare the instantaneous waveform of the AC output voltage with that of a desired reference voltage, and to cause the half-bridge inverter to switch in such manner as to force the frequency, magnitude and waveshape of the AC output voltage resulting from that half-bridge inverter to conform to those of the desired reference voltage.

As an overall result, the AC output voltage resulting from each half-bridge inverter can be made to have substantially any desired phase, frequency, magnitude and/or waveshape—without incurring any substantial power dissipation within the DC-to-AC converter.

In the preferred embodiment, the reference voltage is provided in the form of a sinusoidal three-phase voltage, the magnitude of which is made to increase in direct proportion to its frequency.

DESCRIPTION OF THE PREFERRED EMBODIMENT

Details of Construction of the AC-to-DC Converter

Figure 1:
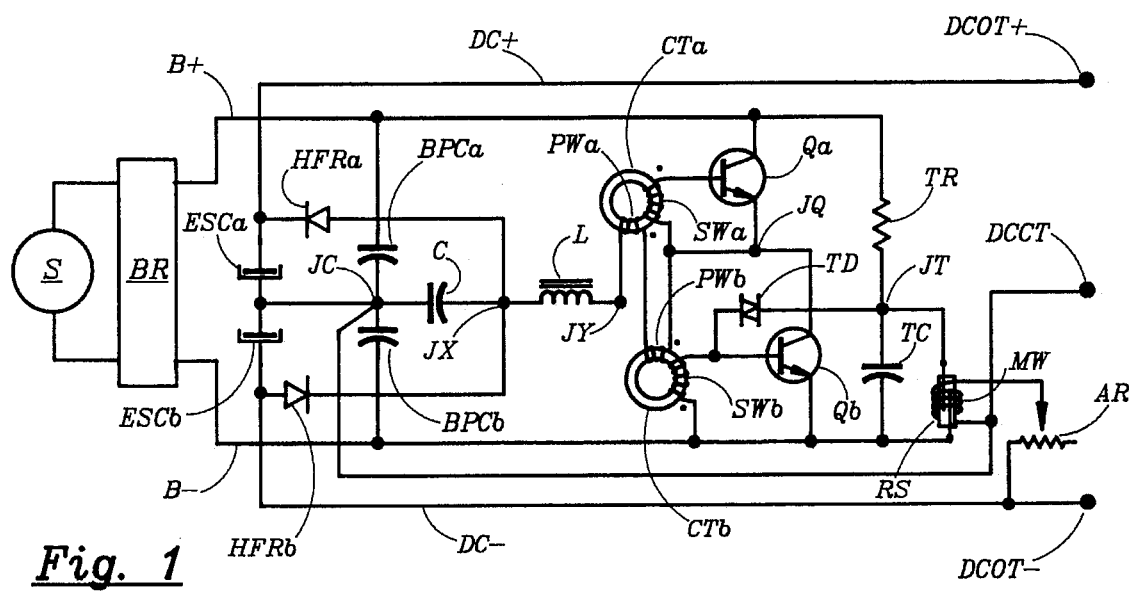
FIG. 1 schematically illustrates the AC-to-DC converter circuit operative to generate the adjustable constant-magnitude DC voltage used to power the DC-to-AC converter.

In the AC-to-DC converter of FIG. 1, a source S provides ordinary 120 Volt/60 Hz power line voltage to a bridge rectifier BR, the DC output of which is applied between a B+ bus and a B− bus, with the B+ bus being of positive polarity.

A first high-frequency bypass capacitor BPCa is connected between the B+ bus and a junction JC; and a second high-frequency bypass capacitor BPCb is connected between junction JC and the B− bus.

A first switching transistor Qa is connected with its collector to the B+ bus and with its emitter to a junction JQ; a second switching transistor Qb is connected with its collector to junction JQ and with its emitter to the B− bus.

A tank capacitor C is connected between junction JC and a junction JX; a tank inductor L is connected between junction JX and a junction JY; and primary windings PWa and PWb of positive feedback saturable current transformers CTa and CTb, respectively, are connected in series between junction JY and junction JQ.

Secondary winding SWa of transformer CTa is connected between the base and emitter of transistor Qa; secondary winding SWb of transformer CTb is connected between the base and the emitter of transistor Qb.

A first energy-storing capacitor ESCa is connected between junction JC and a positive DC bus DC+; and a second energy-storing capacitor ESCb is connected between junction JC and a negative DC bus DC−.

A first high frequency rectifier HFRa is connected with its anode to junction JX and with its cathode to the DC+ bus. A second high frequency rectifier is connected with its cathode to junction JX and with its anode to the DC− bus.

A trigger resistor TR is connected between the B+ bus and a junction JT; and a trigger capacitor TC is connected between junction JT and the B− bus. A trigger Diac TD is connected between junction JT and the base of transistor Qb.

The contactor terminals of a magnetic reed switch RS are connected across trigger capacitor TC, which is to say: between junction JT and the B− bus. Around the reed switch is placed a magnetizing winding MW, the terminals of which are connected in series with an adjustable resistor AR to form a series-combination, and this series-combination is connected between junction JC and the DC− bus.

The DC output voltage of the AC-to-DC converter of FIG. 1 is provided across DC output terminals DCOT+ and DCOT−; which DC output terminals are connected with the DC+ bus and the DC− bus, respectively.

An output DC center-tap DCCT is connected directly with junction JC.

Details of Operation of the AC-to-DC Converter

Figure 2:
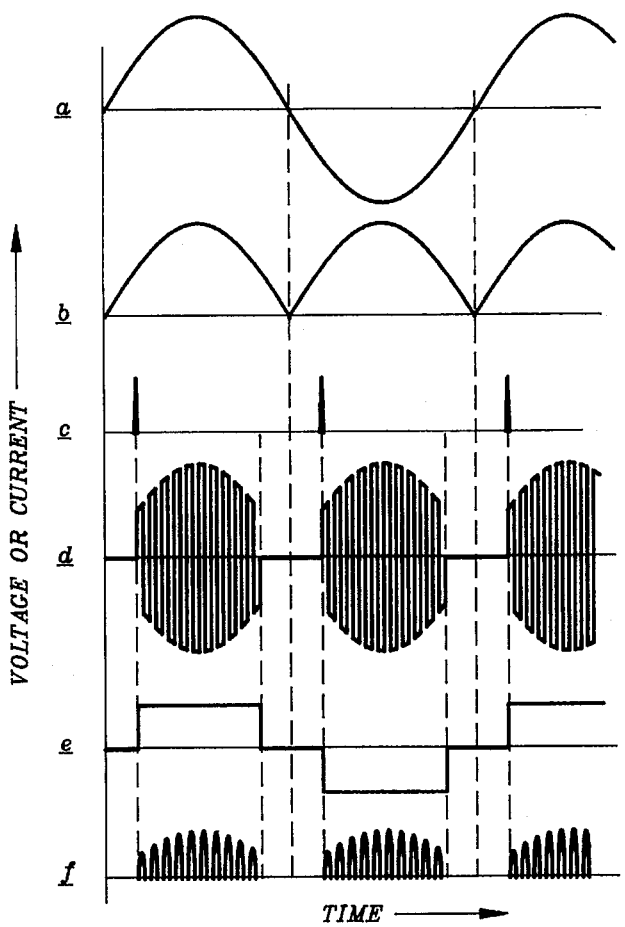
FIG. 2 illustrates various voltage and current waveforms associated with the circuit of FIG. 1.

The detailed operation of the AC-to-DC converter circuit of FIG. 1 may best be understood with reference to the various waveforms of FIG. 2, wherein:

FIG. 2a shows the waveform of the 120 Volt/60 Hz AC voltage provided from source S;

FIG. 2b shows the waveform of the full-wave-rectified 120 Volt/60 Hz AC voltage;

FIG. 2c shows the trigger pulses provided to the base of transistor Qb;

FIG. 2d shows the waveform of the high-frequency voltage provided between junctions JY and JC;

FIG. 2e shows the waveform of the current drawn from the 120 Volt/60 Hz AC voltage source S; and FIG. 2f shows the waveform of the charging current provided to one of the energy-storing capacitors ESCa/ ESCb.

The circuit arrangement of FIG. 1 comprises a self-oscillating half-bridge inverter; which inverter consists principally of the following components: bypass capacitors BPCa/BPCb, transistors Qa/Qb, and positive feedback current transformers CTa/CTb. The operation of such a self-oscillating half-bridge inverter is well known and is described in various ways in Re. U.S. Pat. Nos. 31,758, 4,506,318 and 4,581,562 to Nilssen.

The output of this half-bridge inverter is provided between junctions JC and JY and is illustrated in FIG. 2d as being an amplitude-modulated high-frequency squarewave voltage. Connected with the inverter's output, between junctions JC and JY, is a series-tuned L-C circuit consisting of tank inductor L and tank capacitor C. This series-tuned L-C circuit is series-resonant at or near the fundamental frequency (30 kHz) of the inverter's amplitude-modulated high-frequency squarewave output voltage.

As long as indeed provided, each of the trigger pulses of FIG. 2c occurs at a point approximately 30 degrees after the beginning of each sinusoidally-shaped DC supply voltage pulse of FIG. 2b. Since the inverter is arranged to cease oscillation whenever the instantaneous magnitude of its DC supply voltage falls below the level associated with a point just a little less than 30 degrees before the end of each sinusoidally-shaped DC supply voltage pulse, the resulting inverter output voltage will be as illustrated in FIG. 2d; which output voltage results in a current-draw from the AC voltage source (S) as illustrated in FIG. 2e and in a charging-current provided to energy-storing capacitors ESC1/ESC2 as illustrated in FIG. 2f.

More particularly, being excited by the intermittent amplitude-modulated 30 kHz squarewave voltage of FIG. 2d, and being series-resonant at or near the 30 kHz fundamental frequency of this squarewave voltage, the voltage developed across the tank capacitor (C) will (by way of so-called Q-multiplication) increase in magnitude until it gets limited by loading; which means that it will increase to the point of providing substantial charging current to energy-storing capacitors ESCa and ESCb.

In turn, as long as the inverter operates to produce the output voltage indicated by FIG. 2d, the magnitude of the DC voltage developing across energy-storing capacitors ESCa and ESCb will increase until one or the other of the following events occurs:

i) the current drain caused by DC load means DCLM equals the average charging current being provided from the inverter's output by way of the series-resonant L-C circuit;

ii) the magnitude of the voltage across energy-storing capacitor ESCb gets to be so high as to cause enough current to pass through magnetizing winding MW to cause reed switch RS to close, thereby causing the inverter to stop operation.

Thus, as long as the AC-to-DC converter of FIG. 1 is loaded at or beyond a certain level, the magnitude of the DC output voltage (which exists between DC output terminals DCOT+ and DCOT−) is either at or below a certain predetermined magnitude (which is determined by the setting of adjustable resistor AR), and the inverter then operates in the intermittently continuous manner shown in FIG. 2d.

On the other hand, if the AC-to-DC converter is loaded below said certain level, the magnitude of the DC output voltage will gradually increase until it exceeds the predetermined level. At that point the reed switch closes and the inverter ceases operation, thereby ceasing altogether to provide output.

Thereafter, the magnitude of the DC output voltage will gradually decrease until the amount of current flowing through magnetizing winding MW gets to be so low as to cause reed switch RS to open, thereby to cause the inverter to start operating again, thereby to cause the magnitude of the DC output voltage to start increasing again.

In other words, when loaded to or beyond a certain point, the inverter in the AC-to-DC converter will continuously operate in the (120 Hz) interrupted manner indicated by FIG. 2d; whereas, when loaded below that certain point, the inverter will interruptedly operate in the interrupted manner indicated by FIG. 2d (i.e., it will operate in a doubly interrupted manner).

While the rate of interruption of the inverter's output voltage is a constant 120 Hz (see FIG. 2d), the frequency with which this constant-rate 120 Hz interruption is started, stopped, re-started, re-stopped, etc.) depends on the degree of loading applied to DC output terminals DCOT+/DCOT−, as well as on the degree of hysteresis built into the magnetic reed switch: the smaller the degree of hysteresis, the higher the rate of interruption, and vice versa; the lower the loading, the lower the rate of interruption, and vice versa.

Details of Construction of the DC-to-AC Converter

Figure 3:
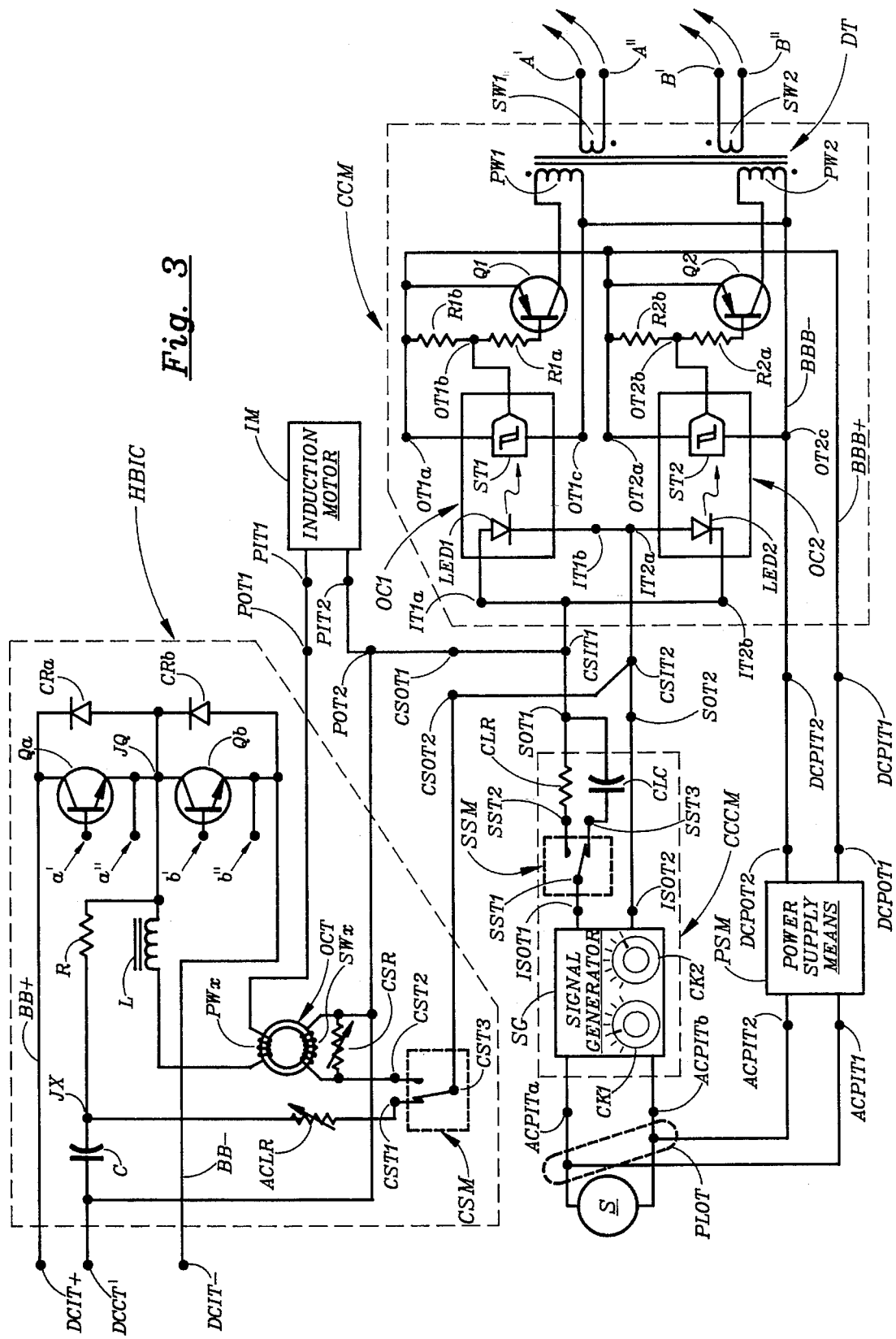
FIG. 3 schematically illustrates the DC-to-AC converter circuit operative to generate an output AC voltage of controllable phase, frequency, magnitude and waveshape.

The DC-to-AC converter is illustrated in FIG. 3 and comprises four principal component parts: i) a half-bridge inverter circuit HBIC, ii) a comparator circuit means CCM, iii) a controllable control current means CCCM, and iv) a power supply means PSM.

Half-bridge inverter circuit HBIC has three DC power input terminals: DCIT+, DCIT− and DCCT'; it has two power output terminals POT1 and POT2, which are connected with power input terminals PIT1 and PIT2 of an induction motor IM; it has two control signal output terminals CSOT1 and CSOT2; and it has two pairs of drive input terminals a'/a" and b'/b".

Comparator circuit means CCM has two DC power input terminals DCPIT1 and DCPIT2; it has two control signal input terminals CSIT1 and CSIT2; and it has two pairs of drive output terminals A'/A" and B'/B".

Controllable control current means CCCM has two AC power input terminals ACPITa and ACPITb; and it has two signal output terminals SOT1 and SOT2.

Power supply means PSM has two AC power input terminals ACPIT1 and ACPIT2; and it has two DC power output terminals DCPOT1 and DCPOT2.

DC power input terminals DCIT+, DCIT− and DCCT' of half-bridge inverter circuit HBIC are respectively connected with DC output terminals DCOT+, DCOT− and DCCT of the AC-to-DC converter of FIG. 1. Power output terminals POT1 and POT2 are respectively connected with power input terminals PIT1 and PIT2 of induction motor IM. Control signal output terminals CSOT1 and CSOT2 are respectively connected with control signal input terminals CSIT1 and CSIT2 of comparator circuit means CCM. And drive input terminals a', a", b' and b" are respectively connected with drive output terminals A', A", B' and B".

DC power input terminals DCPIT1 and DCPIT2 of comparator circuit means CCM are respectively connected with DC power output terminals DCPOT1 and DCPOT2 of power supply means PSM. Control signal input terminals CSIT1 and CSIT2 are connected with signal output terminals SOT1 and SOT2, respectively, of controllable control current means CCCM.

Controllable control current means CCCM is connected with its AC power input terminals ACPITa and ACPITb with power line output terminals PLOT of source S; and it is connected with its signal output terminals SOT1 and SOT2 to control signal input terminals CSIT1 and CSIT2, respectively, of comparator circuit means CCM.

Power supply means PSM is connected with its AC power input terminals ACPIT1 and ACPIT2 with power line output terminals PLOT of source S; and it is connected with its DC power output terminals DCPOT1 and DCPOT2 to DC power input terminals DCPIT1 and DCPIT2, respectively, of comparator circuit means CCM.

In half-bridge inverter circuit HBIC, the DCIT+ terminal is connected with a BB+ bus and the DCIT− terminal is connected with a BB− bus.

In HBIC, a first transistor Qa is connected with its collector to the BB+ bus and with its emitter to a junction JQ; and a second transistor Qb is connected with its collector to junction JQ and with its emitter to the BB− bus. A first commutating rectifier CRa is connected with its cathode to the BB+ bus and with its anode to junction JQ; and a commutating rectifier CRb is connected with its cathode to junction JQ and with its anode to the BB− bus.

An inductor L is connected between junction JQ and power output terminal POT1 by way of primary winding PWx of output current transformer OCT. Power output terminal POT2 is connected directly with DC center-tap DCCT'.

A resistor R is connected between junction JQ and a junction JX; and a capacitor C is connected between junction JX and DC center-tap DCCT'.

A control switch means CSM has three control switch terminals CST1, CST2 and CST3.

An adjustable current-limiting resistor ACLR is connected between junction JX and first control switch terminal CST1.

Output current transformer OCT has a secondary winding SWx connected between power output terminal POT2 and second control switch terminal CST2. A current-shunting resistor CSR is connected between terminals POT2 and CST2.

DC center-tap DCCT' is connected with control signal output terminal CSOT1; and control switch terminal CST3 is connected with control signal output terminal CSOT2.

Comparator circuit means CCM comprises: i) a first opto-coupler OC1 having input terminals IT1a and IT1b, and output terminals OT1a, OT1b and OT1c; and ii) a second opto-coupler having input terminals IT2a and IT2b, and output terminals OT2a, OT2b and OT2c.

The anode and cathode of a first light-emitting diode LED1 are connected with input terminal IT1a and IT1b, respectively; the anode and cathode of a second light-emitting diode LED2 are connected with input terminals IT2a and IT2b, respectively.

A first Schmitt trigger ST1 has a positive voltage terminal, a controlled output terminal, and a negative voltage terminal; which terminals are connected with output terminals OT1a, OT1b and OT1c, respectively.

A second Schmitt trigger ST2 also has a positive voltage terminal, a controlled output terminal, and a negative voltage terminal; which terminals are connected with output terminals OT2a, OT2b and OT2c, respectively.

Input terminals IT1a and IT2b are connected together, and so are input terminals IT1b and IT2a as well. The IT1a/IT2b and the IT1b/IT2a terminals are connected with control signal input terminals CSIT1 and CSIT2, respectively.

Output terminal OT1a is connected with output terminal OT2a; which OT1a/OT2a terminals are jointly connected directly with a BBB+ bus. Output terminal OT1c is connected with output terminal OT2c; which OT1c/OT2c terminals are jointly connected directly with a BBB− bus. The BBB+ bus and the BBB− bus are connected with DC power input terminals DCPIT1 and DCPIT2, respectively.

A first PNP transistor Q1 is connected with its emitter to the BBB+ bus; the base of transistor Q1 is connected with output terminal OT1b of opto-coupler OC1 by way of a resistor R1a; and the collector of transistor Q1 is connected with the BBB− bus by way of a first primary winding PW1 of a drive transformer DT. A resistor R1b is connected between output terminals OT1a and OT1b.

A second PNP transistor Q2 is connected with its emitter to the BBB+ bus; the base of transistor Q2 is connected with output terminal OT2b of opto-coupler OC2 by way of a resistor R2a; and the collector of transistor Q2 is connected with the BBB− bus by way of a second primary winding PW2 of drive transformer DT. A resistor R2b is connected between output terminals OT2a and OT2b.

A first secondary winding SW1 of drive transformer DT is connected between drive output terminals A' and A"; and a second secondary winding SW2 of drive transformer DT is connected between drive output terminals B' and B".

Controllable control current means CCCM comprises a signal generator SG that is connected between AC power input terminals ACPITa/ACPITb and intermediary signal output terminals ISOT1 and ISOT2. Signal generator SG provides an AC signal voltage across terminals ISOT1 and ISOT2, and it has: i) a first control knob CK1 operative to permit adjustment of the frequency of the AC signal voltage, and ii) a second control knob CK2 operative to permit adjustment of the waveform of the AC signal voltage.

Intermediary signal output terminal ISOT1 is connected with signal switch terminal SST1 of a signal switch means SSM, whose other signal switch terminals SST2 and SST3 are, respectively, connected with signal output terminal SOT1 by way of a current-limiting resistor CLR and a current-limiting capacitor CLC. Terminal ISOT2 is directly connected with terminal SOT2.

Power supply means PSM is connected between AC power input terminals ACPIT1/ACPIT2 and DC power output terminals DCPOT1/DCPOT2; and provides a DC voltage therebetween terminals DCPOT1 and DCPOT2, with terminal DCPOT1 being of positive polarity.

Details of Operation of the DC-to-AC Converter

Figure 4:
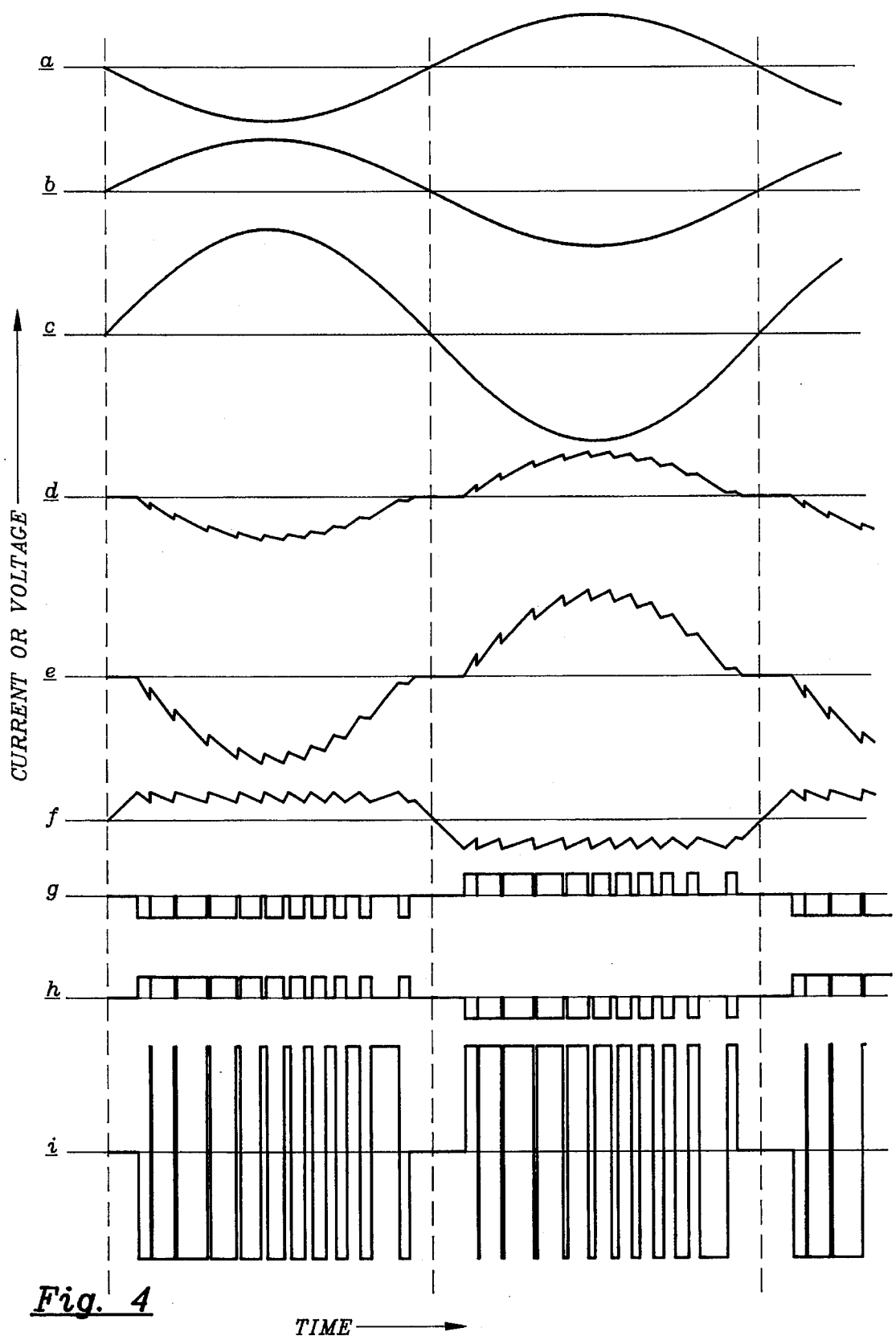
FIG. 4 illustrates various voltage and current waveforms associated with the circuit of FIG. 3.

The detailed operation of the DC-to-AC converter circuit of FIG. 3 may best be understood with reference to the various voltage and current waveforms of FIG. 4, wherein:

FIG. 4a shows the waveform of the AC output voltage desired across power output terminals POT1/POT2;

FIG. 4b shows the waveform of a reference AC signal voltage provided at intermediary signal output terminal ISOT1, as referenced to terminals ISOT2/SOT2/DCCT'/POT2, which four terminals are all at the same electrical potential since they are all connected together;

FIG. 4c shows the waveform of the current provided from terminal SOT1 to terminal CSIT1 in response to the reference AC signal voltage, which current is hereinafter sometimes referred to as the reference current;

FIG. 4d shows the waveform of the voltage developed at junction JX; which voltage is approximately equal to the voltage provided at power output terminal POT1 as referenced to terminals ISOT2/SOT2/DCCT'/POT2;

FIG. 4e shows the waveform of the current flowing into control terminal CSIT1 in response to the AC voltage present at junction JX, which current is hereinafter sometimes referred to as the response current;

FIG. 4f shows the net current flowing into control terminal CSIT1, which net current is the sum of the currents depicted in FIGS. 4c and 4e;

FIG. 4g shows the waveform of the voltage provided at drive input terminal a' as referenced to drive input terminal a";

FIG. 4h shows the waveform of the voltage provided at drive input terminal b' as referenced to drive input terminal b"; and FIG. 4i shows the waveform of the corresponding pulse-ratio-modulated squarewave voltage provided at junction JQ, also as referenced to terminals ISOT2/SOT2/DCCT'/POT2.

In the DC-to-AC converter of FIG. 3, the half-bridge inverter circuit HBIC simply operates in such manner as to alternatingly connect junction JQ with the BB+ bus and the BB− bus, with the particular connection being determined by the nature of the drive voltages provided to the bases of transistors Qa and Qb. In turn, these drive voltages are determined by action of comparator circuit means CCM in response to the current being fed through its control signal input terminals CSIT1/CSIT2.

In particular and by way of illustration, a positive current fed into terminal CSIT1 causes light-emitting diode LED1 to emit light, thereby activating Schmitt trigger ST1. With Schmitt trigger ST1 activated, transistor Q1 is caused to conduct, thereby placing a DC voltage across primary winding PW1 of drive transformer DT—with the positive polarity of this DC voltage being at the collector of transistor Q1. In turn, this DC voltage will appear across secondary windings SW1 and SW2 of drive transformer DT, thereby causing a positive base voltage on transistor Qb and a negative base voltage on transistor Qa.

In other words, with a positive current flowing into terminal CSIT1 of comparator circuit means CCM, transistor Qb is caused to conduct. Correspondingly, with a positive current flowing into terminal CSIT2, transistor Qa is caused to conduct.

In overall operation, the DC-to-AC converter of FIG. 3 operates as follows.

The frequency and the waveshape of the AC output voltage desired to be provided across power output terminals POT1/POT2 is selected by way of control knobs CK1 and CK2 on signal generator SG.

The relative magnitude of the desired AC output voltage is selected by way of adjustable current-limiting resistor ACLR of inverter circuit HBIC.

In the particular case illustrated by FIG. 4, the desired AC output voltage, which is illustrated by FIG. 4a, has a sinusoidal waveshape, a frequency of about 75 Hz, and a peak magnitude of about 212 Volt (which corresponds to an RMS magnitude of about 150 Volt); which results in the choice of an AC reference voltage like that depicted in FIG. 4b.

(To permit the output voltage to attain a peak magnitude of 212 Volt, it is necessary first to make certain that the magnitude of the DC supply voltage is adequately large. Hence, adjustable resistor AR of the AC-to-DC converter of FIG. 1 is adjusted such as to make the magnitude of the DC voltage developed across each of energy storing capacitors ESCa/ESCb equal to at least 212 Volt.)

The chosen AC reference voltage causes a proportional reference current (illustrated by FIG. 4c) to flow into control terminal CSIT1 of comparator CCM, the proportionality between the reference voltage and the resulting reference current being determined by the rectance of current-limiting capacitor CLC.

By way of comparator CCM, any substantial change in the magnitude of the reference current acts to cause one of the inverter's switching transistors Qa/Qb to become conductive, thereby to cause the voltage at junction JX to change in such a direction as to provide to control terminal CSIT1 a change in the magnitude of the response current provided from junction JX; which change will be of such direction as to subtract from the change in the magnitude of the reference current.

Thus, the action of comparator CCM is such as to force the waveshape of the response current to be substantially equal to that of the reference current; which means that the magnitude of the voltage at junction JX will be forced on an ongoing basis to conform to that of the AC reference voltage.

In response to the reference current of FIG. 4c, as a direct result of the actions of comparator CCM, the DC-to-AC converter of FIG. 3 will exhibit the voltages and currents depicted by the different waveforms of FIG. 4.

Details of Construction of a Three-Phase AC Generator

Figure 5:
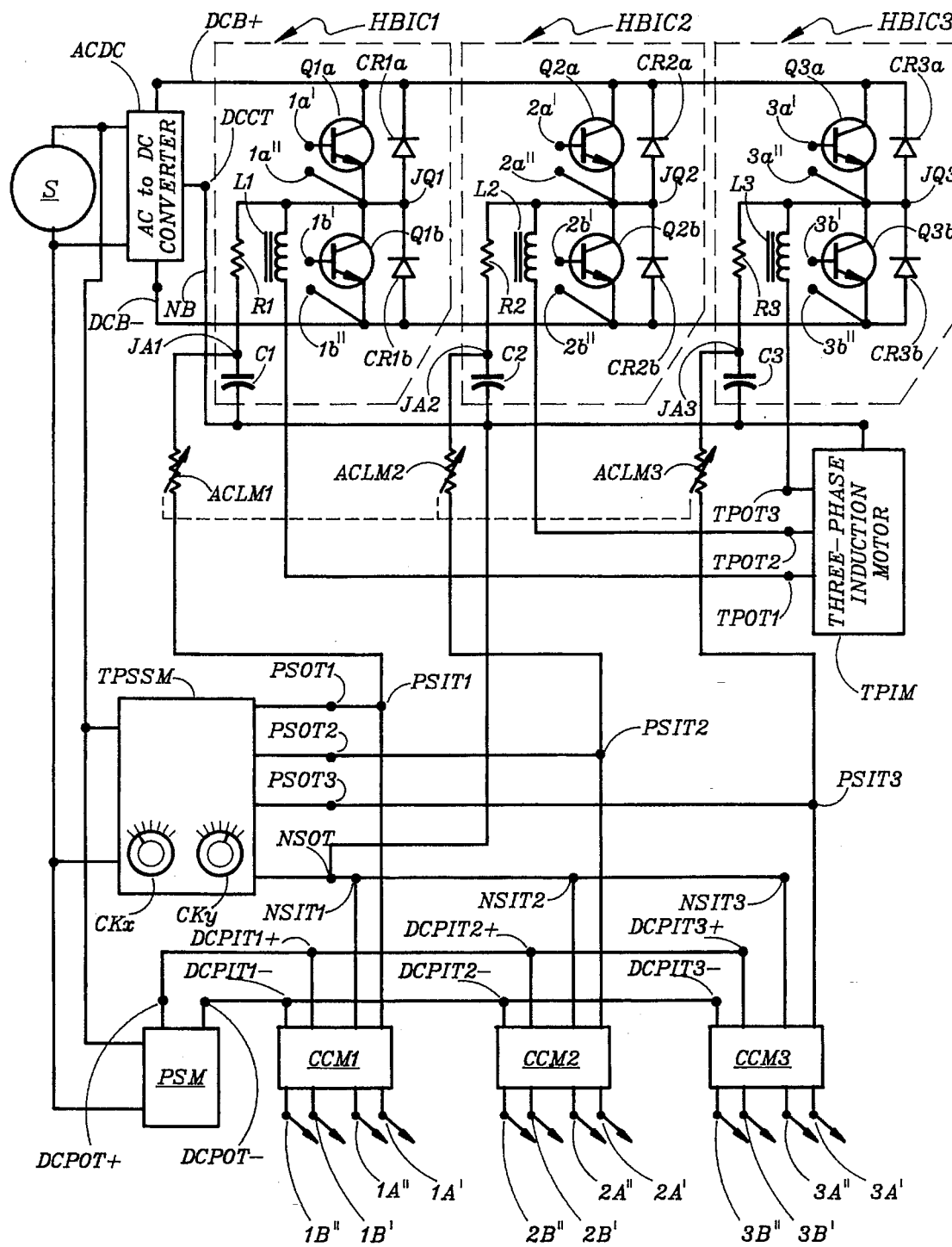
FIG. 5 schematically illustrates the application of the DC-to-AC converter circuit of FIG. 3 to generate a three-phase AC voltage of controllable frequency, magnitude and waveshape.

FIG. 5 schematically illustrates the combined application of the AC-to-DC converter circuit of FIG. 1 with three DC-to-AC converters of the type illustrated by FIG. 3, thereby to provide three independent separately controllable AC output voltages; which, since actually being controlled such as to be synchronous with one another and in 120 degree mutual phase relationships, will constitute a controllable three-phase AC output voltage. Thus, in overall function, the combination circuit and block diagram of FIG. 5 describes a controllable electronic three-phase AC generator powered from an ordinary single-phase electric utility power line.

In FIG. 5, source S represents an ordinary electric utility power line, the 120 Volt/60 Hz power line voltage of which is provided to an AC-to-DC converter ACDC like that of FIG. 1. The DC output from this AC-to-DC converter is provided between a positive DC bus DCB+ and a negative DC bus DCB−, and has a DC center-tap DCCT connected with a neutral bus NB. These buses are connected with three half-bridge inverter circuits HBIC1, HBIC2 and HBIC3; which provide their AC output voltages between neutral bus NB and, respectively, three-phase output terminals TPOT1, TPOT2 and TPOT3.

In half-bridge inverter circuit HBIC1, a transistor Q1a is connected with its collector with the DCB+ bus and with its emitter to a junction JQ1; and a transistor Q1b is connected with its collector to junction JQ1 and with its emitter to the DCB− bus. A commutating rectifier CR1a is connected with its cathode to the DCB+ bus and with its anode to junction JQ1; and a commutating rectifier CR1b is connected with its cathode to junction JQ1 and with its anode to the DCB− bus. An inductor L1 is connected between junction JQ1 and three-phase output terminal TPOT1; a resistor R1 is connected between junction JQ1 and an auxiliary junction JA1; a capacitor C1 is connected between junction JA1 and neutral bus NB.

Transistor Q1a has two drive input terminals 1a' and 1a" connected respectively with its base and emitter; transistor Q1b has two drive input terminals 1b' and 1b" connected respectively with its base and emitter.

In half-bridge inverter circuit HBIC2, a transistor Q2a is connected with its collector with the DCB+ bus and with its emitter to a junction JQ2; and a transistor Q2b is connected with its collector to junction JQ2 and with its emitter to the DCB− bus. A commutating rectifier CR2a is connected with its cathode to the DCB+ bus and with its anode to junction JQ2; and a commutating rectifier CR2b is connected with its cathode to junction JQ2 and with its anode to the DCB− bus. An inductor L2 is connected between junction JQ2 and three-phase output terminal TPOT2; a resistor R2 is connected between junction JQ2 and an auxiliary junction JA2; a capacitor C2 is connected between junction JA2 and neutral bus NB.

Transistor Q2a has two drive input terminals 2a' and 2a" connected respectively with its base and emitter; transistor Q2b has two drive input terminals 2b' and 2b" connected respectively with its base and emitter.

In half-bridge inverter circuit HBIC3, a transistor Q3a is connected with its collector with the DCB+ bus and with its emitter to a junction JQ3; and a transistor Q3b is connected with its collector to junction JQ3 and with its emitter to the DCB− bus. A commutating rectifier CR3a is connected with its cathode to the DCB+ bus and with its anode to junction JQ3; and a commutating rectifier CR3b is connected with its cathode to junction JQ3 and with its anode to the DCB− bus. An inductor L3 is connected between junction JQ3 and three-phase output terminal TPOT3; a resistor R3 is connected between junction JQ3 and an auxiliary junction JA3; a capacitor C3 is connected between junction JA3 and neutral bus NB.

Transistor Q3a has two drive input terminals 3a' and 3a" connected respectively with its base and emitter; transistor Q3b has two drive input terminals 3b' and 3b" connected respectively with its base and emitter.

A three-phase induction motor TPIM is connected with three-phase output terminals TPOT1, TPOT2 and TPOT3, as well as with neutral bus NB.

Source S also provides 120 Volt/60 Hz power line voltage to a three-phase signal source means TPSSM; which signal source means has three phased signal output terminals PSOT1, PSOT2 and PSOT3, as well as a neutral signal output terminal NSOT. Also, TPSSM has two control knobs CKx and CKy.

Phased signal output terminals PSOT1, PSOT2 and PSOT3 are connected with phased signal input terminals PSIT1, PSIT2 and PSIT3 of comparator circuit means CCM1, CCM2 and CCM3, all respectively; while neutral signal output terminal NSOT is connected with neutral signal input terminals NSIT1, NSIT2 and NSIT3 of comparator circuit means CCM1, CCM2 and CCM3, respectively.

Comparator circuit means CCM1, CCM2 and CCM3 respectively have:

i) positive DC power input terminals DCPIT1+, DCPIT2+ and DCPIT3+, each of which is connected with positive DC power output terminal DCPOT+ of power supply means PSM;

ii) negative DC power input terminals DCPIT1−, DCPIT2− and DCPIT3−, each of which is connected with negative DC power output terminal DCPOT− of power supply means PSM;

iii) drive output terminal pairs 1A'/1A", 2A'/2A" and 3A'/3A" connected with drive input terminal pairs 1a'/1a", 2a'/2a" and 3a'/3a" of half-bridge inverter circuits HBIC1, HBIC2 and HBIC3, all respectively; and iv) drive output terminal pairs 1B'/1B", 2B'/2B" and 3B'/3B" connected with drive input terminal pairs 1b'/1b", 2b'/2b" and 3b'/3b" of half-bridge inverter circuits HBIC1, HBIC2 and HBIC3, all respectively.

Phased signal input terminals PSIT1, PSIT2 and PSIT3 are connected with auxiliary junctions JA1, JA2 and JA3 by way of adjustable current-limiting means ACLM1, ACLM2 and ACLM3, all respectively; and neutral signal output terminal NSOT is connected with neutral bus NB.

Details of Operation of the Three-Phase AC Generator

Figure 6:
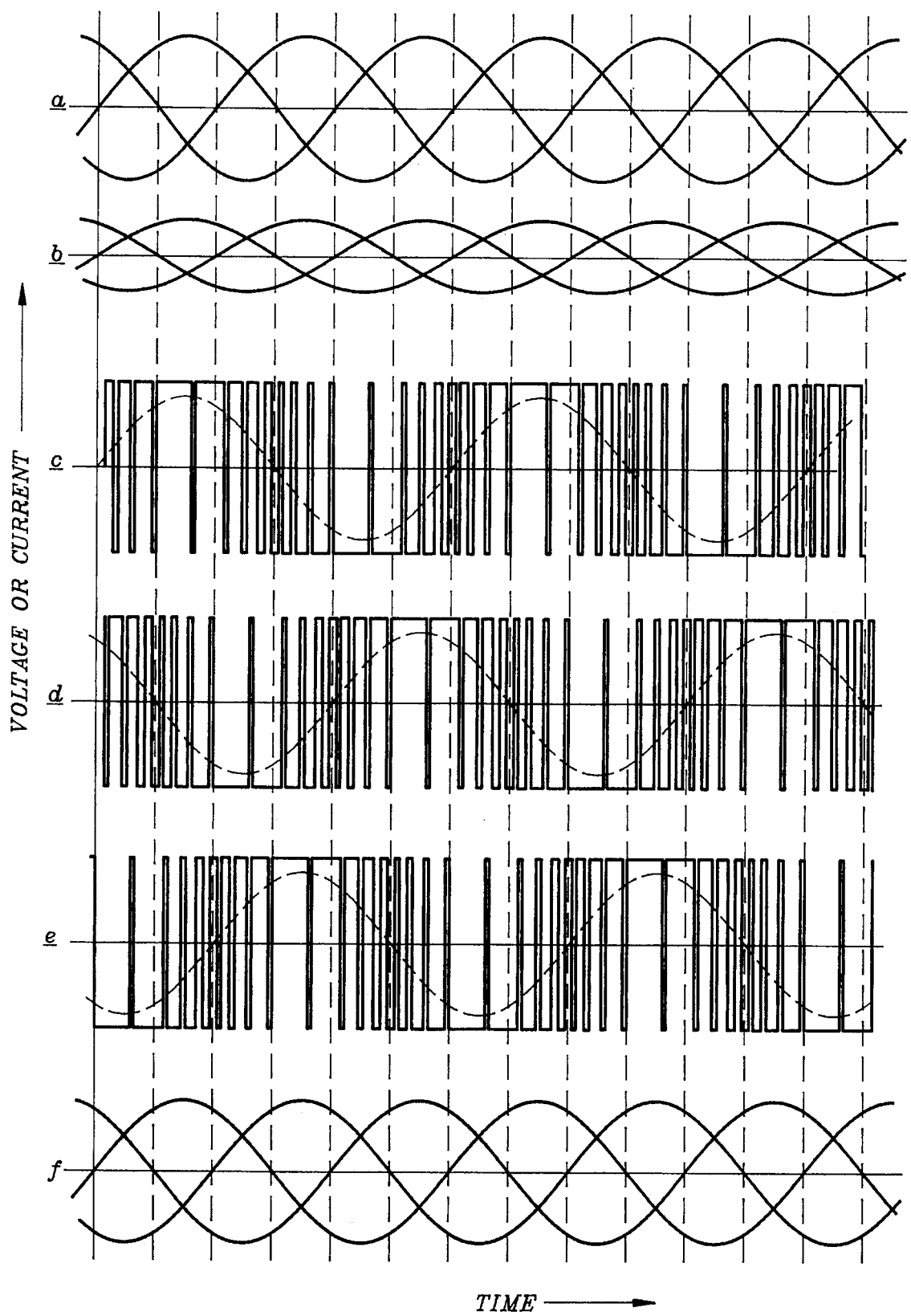
FIG. 6 illustrates various waveforms associated with the circuit arrangement of FIG. 5.

The overall operation of the controllable electronic three-phase generator of FIG. 5 may best be understood with reference to the various voltage and current waveforms of FIG. 6, wherein:

FIG. 6a shows the waveforms of the desired three phased AC output voltages (i.e., the three-phase AC output voltage);

FIG. 6b shows the waveforms of the corresponding three phased AC reference currents provided from the three-phase signal source means TPSSM;

FIG. 6c shows the pulse-ratio-modulated squarewave voltage provided at junction JQ1;

FIG. 6d shows the pulse-ratio-modulated squarewave voltage provided at junction JQ2;

FIG. 6e shows the pulse-ratio-modulated squarewave voltage provided at junction JQ3; and FIG. 6f shows the three phased AC output voltages provided to three-phase induction motor TPIM.

In effect, the circuit of FIG. 5 operates like three of the circuits of FIG. 3. However, in FIG. 5., because the three reference voltages/currents are of equal magnitude and mutually separated by 120 degrees, the net current flowing in the neutral bus will be very small, as long as the resulting motor current is substantially sinusoidal; which indeed is the case.

As indicated by FIG. 6c-e, the average magnitude of the pulse-ratio-modulated voltage provided at each of the three junctions JQ1, JQ2 and JQ3 is equal to the magnitude of the three individual components of the three-phase AC output voltage depicted in FIG. 6f. And, since this average magnitude is sinusoidal, the resulting current will be sinusoidal.

Although the three-phase signal source means may be any suitable variable-frequency three-phase generator, in the preferred embodiment it is actually a low-power three-phase electro-magnetic generator driven by an adjustable-speed DC motor. The three phased outputs from the three-phase generator are then each connected with one of the three phased signal output terminals PSOT1/PSOT2/PSOT3 by way of a current-limiting resistor means, thereby each providing a reference current the magnitude of which is proportional to its frequency.

The speed of the DC motor is adjustable by way of control knob CKx; the relative magnitude of the reference current is adjustable by way of control knob CKy.

Thus, in overall operation, the three-phase AC generator of FIG. 5 functions such as to provide a substantially sinusoidal three-phase AC voltage/current to three-phase induction motor TPIM, with the frequency of this three-phase AC voltage being adjustable via control knob CKx over a range from about 12 Hz to about 120 Hz. As required by the induction motor, the voltage magnitude is automatically varied in proportion with the frequency, thereby to provide for a substantially constant (but setable) product of Volt-seconds per half-cycle. The Volt-second product per half-cycle is adjustable by control-knob CKy.

The level of power required to be provided to phased signal input terminals PSIT1/PSIT2/PSIT3 is only on the order of a few milli-Watts, even if the output power provided to three-phase induction motor TPIM be on the order of kilo-Watts.

Additional Comments a) With respect to the AC/DC converter of FIG. 1, the basic nature of a series-excited parallel-loaded high-Q resonant L-C circuit, when excited by a voltage source, is that of essentially constituting a current source to its parallel-connected load. Moreover, the magnitude of the current provided to the parallel-connected load is substantially proportional to the magnitude of the voltage provided by the series-connected voltage source.

Moreover, when such an L-C circuit is parallel-loaded with a substantially constant-voltage load (such as in instant case), the loading provided by the L-C circuit to the series-connected voltage source is substantially equivalent to a constant-current load. In other words, a parallel-connected constant-magnitude-voltage load converts into a constant-magnitude-current load as seen from the viewpoint of a series-connected source.

b) One result of the above-described basic nature of a high-Q series-excited parallel-loaded resonant L-C circuit is that the magnitude of the charging current provided to the energy-storing capacitors ESC1/ESC2 (see FIG. 2f) is roughly proportional to the magnitude of the inverter output voltage (see FIG. 2d), which in turn in proportional to the magnitude of the inverter's DC supply voltage (see FIG. 2b).

c) Another result is that the magnitude of the current drawn by the half-bridge inverter from its DC voltage supply will be about proportional to the magnitude of the DC voltage present across the energy-storing capacitors.

d) Yet another result is that the magnitude of the current drawn by the series-resonant L-C circuit when powering a constant-voltage parallel-connected load, is substantially constant.

Thus, since—for a given setting of the adjustable resistor (AR)—the magnitude of the voltage on the energy-storing capacitors is substantially constant, the magnitude of the current provided by the inverter into the series-tuned L-C circuit is approximately constant; which, in turn, means that the magnitude of the current drawn by the inverter from its DC supply voltage will be approximately constant—as indicated in FIG. 2e.

e) By virtue of their basic nature, magnetic reed switches have hysteresis. Thus, the magnitude of the current through the magnetizing winding (MW) required for causing the reed switch (RS) to close is higher than the magnitude of the current required to cause it to open.

Within a wide range, the amount of hysteresis can be designed to be just about any degree required. In the preferred embodiment, the hysteresis is about 20%; which implies that the magnitude of the DC output voltage will be regulated to within about plus/minus 10%.

f) By changing the setting of the adjustable resistor (AR), the magnitude of the DC output voltage can likewise be set.

In this connection, it is important to note that the magnitude of the DC output voltage can be set to virtually any level: higher or lower than the peak magnitude of the DC supply voltage, higher or lower than the peak magnitude of the inverter's output voltage, etc.

In instant case, to permit provision of the desired RMS magnitude for the voltage provided to the load means (LM), the magnitude of the DC output voltage is set to about 220 Volt.

g) In the preferred embodiment, the half-bridge inverter of the AC/DC converter circuit of FIG. 1 is so arranged as to oscillate approximately only in the intervals between 30 and 120 degrees, as well as between 210 and 330 degrees, of the 120 Volt/60 Hz supply voltage. As a result, current is drawn from the source only during those intervals; the implication of which is to minimize the third harmonic content of the current drawn from the source, which feature is important in situations where power is provided by a single phase of a three-phase power distribution system—a situation that is frequently encountered in connection with powering fluorescent lighting systems.

h) The current drawn from the power line by the circuit of FIG. 1 is illustrated by FIG. 2e in an idealized form, which would only occur if using perfect components, including an infinitely high Q of the L-C tuned circuit.

With such perfect components—as long as the conduction angle of the current approximately covers the indicated two thirds of the total period of the power line voltage (i.e., the middle 120 degrees out of each half-cycle)—the power factor of the power drawn from the power line would be about 85%.

However, in reality, the waveshape of the current will not have quite as flat a top as is shown in FIG. 2e. Rather, the waveshape will exhibit a slightly curved top—with a raised center. As a result, the power factor of the power actually drawn from the power line will be closer to about 90%.

i) The peak positive magnitude of the net current provided to control terminal CSIT1 of comparator CCM (i.e., the peak positive magnitude of the waveshape of FIG. 4f) is essentially determined by the magnitude of the current required to activate opto-coupler OC1. For the particular opto-coupler used, namely a Motorola H11L1, the magnitude required for activation is about 1.00 milli-Amp. The current magnitude at which de-activation occurs is about 0.75 milli-Amp.

Similarly, the peak negative magnitude of the net current provided to control terminal CSIT1 of comparator CCM (i.e., the peak negative magnitude of the wave shape of FIG. 4f) is essentially determined by the corresponding characteristics of opto-coupler OC2; which in this case also is a Motorola H11L1.

To provide a fairly accurate construction of the desired AC output voltage, it is important that the peak magnitude of the reference current (FIG. 4c) be substantially larger than the magnitude of the current required to activate opto-couplers OC1/OC2. A suitable ratio between the peak magnitude of the reference current and the magnitude of the current required to activate the opto-couplers is about 10:1 or higher; although, for clarity of illustration, the ratio indicated by FIG. 4c and FIG. 4f is only about 4:1.

j) In FIG. 3, in the position indicated by signal switch means SSM, the magnitude of the reference current will increase in proportion with its frequency; which means that the magnitude of the AC voltage provided at terminals POT1 and POT2 will be directly proportional to its frequency. This feature is useful in connection with controlling the speed of an induction motor; in which case, as the frequency of the voltage applied to the motor is increased in order to increase motor speed, the required voltage magnitude should be proportionally increased as well.

k) By making control switch means CSM provide for terminal CST3 to be connected with terminal CST2 instead of terminal CST1, comparator CCM will automatically control the AC output voltage in such manner as to attain a desired current waveform; which current waveform will now conform with the waveform of the reference AC signal voltage provided from signal generator SG.

However, in order not to have the current-magnitude automatically increase with frequency, it is now desirable to use signal switch means SSM to switch-in current-limiting resistor CLR in place of current-limiting capacitor CLC.

l) The purpose of capacitor C is that of providing for an integrating or averaging effect, thereby ensuring that the voltage across capacitor C constitutes a measure of the average voltage provided at junction JQ, with the averaging taking place over a period corresponding to the time-constant RC of the combination of resistor R and capacitor C. Thus, the RC time-constant should be small compared with the period of the AC output voltage of the highest desired frequency.

m) The purpose of inductor L is also that of providing an integration or averaging effect. The inductance of L should be such that the time-constant of L in combination with the load provided across output terminals POT1 and POT2 is short in comparison with the period of the AC output voltage of the highest desired frequency.

n) Due to the presence of inductor L, commutating rectifiers CRa and CRb are manifestly required. They permit the inductive current of inductor L to continue to flow after one of the transistors (Qa or Qb) has been rendered non-conductive—without having to make the other transistor (Qb or Qa, respectively) conductive.

o) Instead of using opto-couplers (OC1/OC2) as the principal components of comparator circuit means CCM, since electrical isolation is already provided-for in the form of drive transformer DT, any number of other means may be used. For instance, it would be entirely feasible to use a high-gain differential amplifier in place of the two opto-couplers.

p) In FIG. 3, for a given frequency-setting on control knob CK1, the setting of adjustable current-limiting resistor ACLR determines the magnitude of the AC voltage provided at power output terminals POT1 and POT2. Thus, while basic control of the speed of induction motor IM is accomplished by adjustment of the frequency control knob CK1, for a given frequency (or motor speed), control of the power factor with which the motor draws power from power output terminals POT1 and POT2 is determined by the setting of ACLR.

In other words, in most situations, the most efficient way of powering a given induction motor at a given speed and load involves the setting of the basic frequency of the AC output voltage by way of control knob CK1 as well as adjustment of the magnitude of the AC output voltage by way of adjustable current-limiting resistor ACLR. However, as ACLR is adjusted for optimum power factor, there is apt to result a second order effect on motor speed; which second order effect may be compensated-for by a re-adjustment of control knob CK1.

q) Substantially all the comments made above in connection with the single-phase AC voltage generator of FIG. 3 and the ordinary single-phase induction motor powered therefrom apply as well to the three-phase AC voltage generator of FIG. 5 and the ordinary three-phase induction motor powered from it.

r) Instead of attaining them by way of the analog-type "bang-bang" feedback scheme used in the arrangements of FIGS. 3 and 5, the pulse-ratio-modulated or pulse-width-modulated squarewave voltages provided at junctions JQ, JQ1, JQ2 and JQ3 thereof can be attained by way of providing the base-emitter drive signals from a relatively simple pulse generator not depending on feedback. In this case, it would simply be necessary to program that pulse generator to provide base-emitter drive signals such as to result in pulse-ratio-modulated (or: pulse-width-modulated) voltages having the requisite average magnitudes as well as the requisite frequency-versus-magnitude relationships.

s) The average magnitude of each of the pulse-width-modulated squarewave voltages provided at junctions JQ1, JQ2 and JQ3 varies in a sinusoidal manner, as shown by the dashed sinusoidal waveforms of FIGS. 6c, 6d and 6e. These waveforms represent the three-phase substantially sinusoidal AC voltage provided to three-phase induction motor TPIM, as well as the currents resulting therefrom.

s) With reference to FIG. 5, in half-bridge inverter circuit HBIC1, the combination of elements Q1a and CR1a may be considered as a first electronic switcher having: i) a first switch terminal represented by the junction between the cathode of rectifier CR1a and the collector of transistor Q1a, and ii) a second switch terminal represented by the junction between the anode of rectifier CR1a and the emitter of transistor Q1a. Correspondingly, the combination of elements Q1b and CR1b may be considered as a second electronic switcher having: i) a first switch terminal represented by the junction between the cathode of rectifier CR1b and the collector of transistor Q1b, and ii) a second switch terminal represented by the junction between the anode of rectifier CR1b and the emitter of transistor Q1b. In turn, the combination of the first electronic switcher and the second electronic switcher may be termed a first electronic switching means having a central switched terminal at junction JQ1. Similar descriptions may, of course, be used in connection with each of the three half-bridge inverter circuits HBIC1, HBIC2 and HBIC3.

I claim:

1. An arrangement comprising:

an AC source providing an AC power line voltage at a pair of power line terminals; and a voltage conditioning circuit connected between the power line terminals and a pair of output terminals; the voltage conditioning circuit being: (i) characterized by drawing current from the power line terminals during at least half of the total duration of each half-cycle of the AC power line voltage; and (ii) operative to provide between the output terminals a conditioned voltage characterized by:

(a) having an absolute magnitude that remains substantially constant over an extensive duration, an extensive duration being defined as a duration that is substantially longer than the duration of a complete cycle of the AC power line voltage; and (b) having an instantaneous magnitude alternating, at a relatively high alternation frequency, between a first voltage level and a second voltage level; the relatively high alternation frequency varying periodically at a relatively low modulation frequency; the relatively low modulation frequency being substantially lower than the relatively high alternation frequency.

2. The arrangement of claim 1 wherein: (i) each complete alternation of the conditioned voltage occupies a certain time duration; (ii) the conditioned voltage has an average magnitude defined as being its average magnitude over said certain time duration; and (iii) this average magnitude varies periodically at said relatively low modulation frequency.

3. The arrangement of claim 1 wherein: (i) a periodic output current flows from the output terminals; and (ii) the period of the periodic output current is substantially longer than said certain time duration.

4. The arrangement of claim 1 wherein said substantially constant absolute magnitude is constant to within plus and minus ten percent from a given value.

5. The arrangement of claim 1 wherein the extensive duration is longer than a complete period of the relatively low frequency modulation frequency.

6. An arrangement comprising:

an AC source providing an AC power line voltage at a pair of power line terminals; and a voltage conditioning circuit connected between the power line terminals and a pair of output terminals; the voltage conditioning circuit being operative to: (i) draw current from the power line terminals during at least half of the total duration of each half-cycle of the AC power line voltage; and (ii) provide between the output terminals a conditioned voltage characterized by:

(a) having an absolute magnitude that remains substantially constant over an extensive duration an extensive duration being defined as a duration that is substantially longer than the duration of a complete cycle of the AC power line voltage; and (b) having an instantaneous magnitude that alternates, at a relatively high alternation frequency, between a first voltage level and a second voltage level; each complete alternation of the conditioned voltage occupying a certain time duration; the conditioned voltage having an average magnitude defined as its average magnitude over said certain time duration; the average magnitude varying periodically at a relatively low frequency, thereby representing a periodic voltage of relatively low frequency; the relatively high alternation frequency being substantially higher than said relatively low frequency as well as substantially higher than the frequency of the AC power line voltage.

7. The arrangement of claim 6 wherein: (i) a load is connected between the output terminals; (ii) a periodic current flows through the load; and (iii) the periodic current has a substantially sinusoidal waveshape.

8. The arrangement of claim 6 wherein: (i) a load is connected between the output terminals; (ii) a periodic current flows through the load; and (iii) the absolute value of the instantaneous magnitude of the periodic current is proportional to the absolute value of said periodic voltage of relatively low frequency.

9. The arrangement of claim 6 wherein: (i) the voltage conditioning circuit draws power from the power line terminals; and (ii) the power drawn from the power line terminals is drawn with a high power factor.

10. An arrangement comprising:

an AC source providing an AC power line voltage at a pair of power line terminals;

a pair of output terminals connected with a load; and a voltage conditioning circuit connected between the power line terminals and the output terminals; the voltage conditioning circuit being characterized by:

A. including a pair of DC terminals across which exists a DC voltage;

B. being operative to provide between the output terminals a conditioned voltage characterized by:

(a) having an absolute magnitude that remains substantially constant over an extensive duration, an extensive duration being defined as a duration that is substantially longer than the duration of a complete cycle of the AC power line voltage; and (b) having an instantaneous magnitude that alternates, at a relatively high alternation frequency, between a first voltage level and a second voltage level; each complete alternation of the conditioned voltage occupying a certain time duration; the conditioned voltage having an average magnitude defined as its average magnitude over said certain time duration; the average magnitude varying periodically at a relatively low frequency; the relatively high alternation frequency being substantially higher than said relatively low frequency as well as substantially higher than the frequency of the AC power line voltage; and C. drawing current from the power line terminals during at least half of the total duration of each half-cycle of the AC power line voltage.

11. The arrangement of claim 10 wherein the absolute peak-to-peak magnitude of the conditioned voltage is equal to the absolute magnitude of the DC voltage.

12. An arrangement comprising:

an AC source providing an AC power line voltage at a pair of power line terminals;

AC-to-DC conversion circuitry connected with the power line terminals and operative to provide a DC voltage at a pair of DC terminals; the AC-to-DC conversion circuitry being characterized by including a periodically conducting transistor; and DC-to-AC conversion circuitry connected with the DC terminals and operative to provide a substantially sinusoidal AC output voltage at a pair of AC output terminals; the DC-to-AC circuitry including control circuitry operative to permit control of the frequency and/or the magnitude of the AC output voltage.

13. The arrangement of claim 12 wherein an AC electric motor is connected with the AC output terminals.

* * * * *